US011197665B2

(12) United States Patent
Nicholas et al.

(10) Patent No.: US 11,197,665 B2
(45) Date of Patent: Dec. 14, 2021

(54) NEEDLE RELOAD DEVICE FOR USE WITH ENDOSTITCH DEVICE

(71) Applicant: Covidien LP, Mansfield, MA (US)

(72) Inventors: David A. Nicholas, Trumbull, CT (US); Russell Pribanic, Roxbury, CT (US); Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 177 days.

(21) Appl. No.: 16/419,082

(22) Filed: May 22, 2019

(65) Prior Publication Data

US 2020/0038012 A1 Feb. 6, 2020

Related U.S. Application Data

(60) Provisional application No. 62/714,781, filed on Aug. 6, 2018.

(51) Int. Cl.
*A61B 17/04* (2006.01)
*A61B 17/06* (2006.01)
*A61B 17/062* (2006.01)

(52) U.S. Cl.
CPC ...... *A61B 17/0469* (2013.01); *A61B 17/0482* (2013.01); *A61B 17/062* (2013.01); *A61B 17/06066* (2013.01)

(58) Field of Classification Search
CPC ............ A61B 17/0469; A61B 17/0482; A61B 17/06066; A61B 17/062; A61B 17/06123;
(Continued)

(56) References Cited

U.S. PATENT DOCUMENTS 1,822,330 A 9/1931 Ainslie
2,327,353 A 8/1943 Karle
(Continued)

FOREIGN PATENT DOCUMENTS

DE 4423881 C1 10/1995
EP 0592244 A2 4/1994
(Continued)

OTHER PUBLICATIONS

International Search Report for PCT/US2007/021506 dated Apr. 16, 2008 (2 pgs.).
(Continued)

*Primary Examiner* — Shaun L David
*Assistant Examiner* — Joshua T Hicks
(74) *Attorney, Agent, or Firm* — Carter, DeLuca & Farrell LLP

(57) ABSTRACT

A needle reload device includes a loading assembly including a needle holder pulley and a needle release arm. The needle holder pulley includes a base including first and second portions configured to receive a needle. The needle release arm is transitionable between an engaged state, in which the needle release arm engages the needle holder pulley to inhibit rotation of the needle holder pulley, and a disengaged state, in which the needle release arm is disengaged from the needle holder pulley such that the needle holder pulley is rotatable. When the needle release arm is in the engaged state, the first portion of the needle holder pulley is positioned between jaws of a stitching device, and when the needle release arm is in the disengage state, the second portion of the base of the needle holder pulley is positioned between the jaws.

20 Claims, 5 Drawing Sheets

(58) Field of Classification Search
CPC .......... A61B 17/06114; A61B 17/0625; A61B 2017/0609; A61B 2017/06047; A61B 2090/034; A61B 17/06161; A61B 2017/06142; A61B 2017/2936; A61B 17/0491; A61B 2017/0479; A61B 17/06119; A61B 17/06128; A61B 17/06133; A61B 17/06138
See application file for complete search history.

(56) References Cited

U.S. PATENT DOCUMENTS

| | | |
|---|---|---|
| 3,073,311 A | 1/1963 | Tibbs et al. |
| 3,123,077 A | 3/1964 | Alcamo |
| 4,236,470 A | 12/1980 | Stenson |
| 4,890,615 A | 1/1990 | Caspari et al. |
| 4,923,461 A | 5/1990 | Caspari et al. |
| 4,935,026 A | 6/1990 | McFadden |
| 4,935,027 A | 6/1990 | Yoon |
| 4,957,498 A | 9/1990 | Caspari et al. |
| 5,037,433 A | 8/1991 | Wilk et al. |
| 5,042,707 A | 8/1991 | Taheri |
| 5,080,663 A | 1/1992 | Mills et al. |
| 5,100,421 A | 3/1992 | Christoudias |
| 5,100,430 A | 3/1992 | Avellanet et al. |
| 5,209,747 A | 5/1993 | Knoepfler |
| 5,224,948 A | 7/1993 | Abe et al. |
| 5,271,543 A | 12/1993 | Grant et al. |
| 5,282,806 A | 2/1994 | Haber et al. |
| 5,300,082 A | 4/1994 | Sharpe et al. |
| 5,308,353 A | 5/1994 | Beurrier |
| 5,314,446 A | 5/1994 | Hunter et al. |
| 5,330,502 A | 7/1994 | Hassler et al. |
| 5,336,229 A | 8/1994 | Noda |
| 5,350,391 A | 9/1994 | Iacovelli |
| 5,358,498 A | 10/1994 | Shave |
| 5,374,277 A | 12/1994 | Hassler |
| 5,381,943 A | 1/1995 | Allen et al. |
| 5,387,221 A | 2/1995 | Bisgaard |
| 5,389,103 A | 2/1995 | Melzer et al. |
| 5,391,176 A | 2/1995 | de la Torre |
| 5,403,342 A | 4/1995 | Tovey et al. |
| 5,405,352 A | 4/1995 | Weston |
| 5,409,498 A | 4/1995 | Braddock et al. |
| 5,439,478 A | 8/1995 | Palmer |
| 5,448,989 A | 9/1995 | Heckele |
| 5,454,823 A | 10/1995 | Richardson et al. |
| 5,454,827 A | 10/1995 | Aust et al. |
| 5,465,894 A | 11/1995 | Clark et al. |
| 5,472,446 A | 12/1995 | de la Torre |
| 5,478,344 A | 12/1995 | Stone et al. |
| 5,478,345 A * | 12/1995 | Stone ................ A61B 17/0469 206/339 |
| 5,480,406 A | 1/1996 | Nolan et al. |
| 5,496,334 A | 3/1996 | Klundt et al. |
| 5,527,323 A | 6/1996 | Jervis et al. |
| 5,540,375 A | 7/1996 | Bolanos et al. |
| 5,540,703 A | 7/1996 | Barker, Jr. et al. |
| 5,540,706 A | 7/1996 | Aust et al. |
| 5,549,617 A | 8/1996 | Green et al. |
| 5,549,637 A | 8/1996 | Crainich |
| 5,562,686 A | 10/1996 | Sauer et al. |
| 5,564,615 A | 10/1996 | Bishop et al. |
| 5,571,090 A | 11/1996 | Sherts |
| 5,573,286 A | 11/1996 | Rogozinski |
| 5,575,799 A | 11/1996 | Bolanos et al. |
| 5,582,617 A | 12/1996 | Klieman et al. |
| 5,588,581 A | 12/1996 | Conlon et al. |
| 5,591,181 A | 1/1997 | Stone et al. |
| 5,601,224 A | 2/1997 | Bishop et al. |
| 5,607,095 A | 3/1997 | Smith et al. |
| 5,620,415 A | 4/1997 | Lucey et al. |
| 5,628,756 A | 5/1997 | Barker, Jr. et al. |
| 5,630,825 A | 5/1997 | de la Torre et al. |
| 5,632,751 A | 5/1997 | Piraka |
| 5,634,584 A | 6/1997 | Okorocha et al. |
| 5,643,293 A | 7/1997 | Kogasaka et al. |
| 5,643,294 A | 7/1997 | Tovey et al. |
| 5,662,662 A | 9/1997 | Bishop et al. |
| 5,662,666 A | 9/1997 | Onuki et al. |
| 5,674,229 A | 10/1997 | Tovey et al. |
| 5,674,230 A | 10/1997 | Tovey et al. |
| 5,681,331 A | 10/1997 | de la Torre et al. |
| 5,690,652 A | 11/1997 | Wurster et al. |
| 5,690,653 A | 11/1997 | Richardson et al. |
| 5,702,408 A | 12/1997 | Wales et al. |
| 5,715,942 A | 2/1998 | Li et al. |
| 5,728,107 A | 3/1998 | Zlock et al. |
| 5,728,109 A | 3/1998 | Schulze et al. |
| 5,728,113 A | 3/1998 | Sherts |
| 5,730,747 A | 3/1998 | Ek et al. |
| 5,746,751 A | 5/1998 | Sherts |
| 5,749,828 A | 5/1998 | Solomon et al. |
| 5,749,898 A | 5/1998 | Schulze et al. |
| 5,752,973 A | 5/1998 | Kieturakis |
| 5,755,729 A | 5/1998 | de la Torre et al. |
| 5,759,188 A | 6/1998 | Yoon |
| 5,766,196 A | 6/1998 | Griffiths |
| 5,772,578 A | 6/1998 | Heimberger et al. |
| 5,779,646 A | 7/1998 | Koblish et al. |
| 5,792,153 A | 8/1998 | Swain et al. |
| 5,792,165 A | 8/1998 | Klieman et al. |
| 5,797,537 A | 8/1998 | Oberlin et al. |
| 5,797,927 A | 8/1998 | Yoon |
| 5,797,928 A | 8/1998 | Kogasaka |
| 5,807,241 A | 9/1998 | Heimberger |
| 5,814,054 A | 9/1998 | Kortenbach et al. |
| 5,814,069 A | 9/1998 | Schulze et al. |
| 5,817,119 A | 10/1998 | Klieman et al. |
| 5,827,323 A | 10/1998 | Klieman et al. |
| 5,865,836 A | 2/1999 | Miller |
| 5,871,488 A | 2/1999 | Tovey et al. |
| 5,876,412 A | 3/1999 | Piraka |
| 5,893,592 A | 4/1999 | Schulze et al. |
| 5,897,563 A | 4/1999 | Yoon et al. |
| 5,906,630 A | 5/1999 | Anderhub et al. |
| 5,908,428 A * | 6/1999 | Scirica ............... A61B 17/0469 206/339 |
| 5,911,727 A | 6/1999 | Taylor |
| 5,928,136 A | 7/1999 | Barry |
| 5,931,855 A | 8/1999 | Buncke |
| 5,938,668 A | 8/1999 | Scirica et al. |
| 5,941,430 A | 8/1999 | Kuwabara |
| 5,947,982 A | 9/1999 | Duran |
| 5,951,575 A | 9/1999 | Bolduc et al. |
| 5,954,731 A | 9/1999 | Yoon |
| 5,954,733 A | 9/1999 | Yoon |
| 5,957,937 A | 9/1999 | Yoon |
| 5,980,538 A | 11/1999 | Fuchs et al. |
| 5,984,932 A | 11/1999 | Yoon |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,017,358 A | 1/2000 | Yoon et al. |
| 6,027,522 A | 2/2000 | Palmer |
| 6,051,006 A | 4/2000 | Shluzas et al. |
| 6,071,289 A | 6/2000 | Stefanchik et al. |
| 6,077,287 A | 6/2000 | Taylor et al. |
| 6,080,180 A | 6/2000 | Yoon et al. |
| 6,086,601 A | 7/2000 | Yoon |
| 6,119,913 A | 9/2000 | Adams et al. |
| 6,126,665 A | 10/2000 | Yoon |
| 6,126,666 A | 10/2000 | Trapp et al. |
| 6,139,563 A | 10/2000 | Cosgrove, III et al. |
| 6,143,005 A | 11/2000 | Yoon et al. |
| 6,171,316 B1 | 1/2001 | Kovac et al. |
| 6,206,893 B1 | 3/2001 | Klein et al. |
| 6,214,028 B1 | 4/2001 | Yoon et al. |
| 6,223,100 B1 | 4/2001 | Green |
| 6,224,614 B1 | 5/2001 | Yoon |
| 6,261,307 B1 | 7/2001 | Yoon et al. |
| 6,277,132 B1 | 8/2001 | Brhel |
| 6,319,262 B1 | 11/2001 | Bates et al. |

(56) References Cited

U.S. PATENT DOCUMENTS

| | | |
|---|---|---|
| 6,332,889 B1 | 12/2001 | Sancoff et al. |
| 6,346,111 B1 | 2/2002 | Gordon et al. |
| 6,358,259 B1 | 3/2002 | Swain et al. |
| 6,494,888 B1 | 12/2002 | Laufer et al. |
| 6,506,196 B1 | 1/2003 | Laufer |
| 6,517,539 B1 | 2/2003 | Smith et al. |
| 6,533,796 B1 | 3/2003 | Sauer et al. |
| 6,569,105 B1 | 5/2003 | Kortenbach et al. |
| 6,582,450 B2 | 6/2003 | Ouchi |
| 6,596,015 B1 | 7/2003 | Pitt et al. |
| 6,599,310 B2 | 7/2003 | Leung et al. |
| 6,638,287 B2 | 10/2003 | Danitz et al. |
| 6,663,639 B1 | 12/2003 | Laufer et al. |
| 6,663,641 B1 | 12/2003 | Kovac et al. |
| 6,666,854 B1 | 12/2003 | Lange |
| 6,676,676 B2 | 1/2004 | Danitz et al. |
| 6,695,774 B2 | 2/2004 | Hale et al. |
| 6,719,764 B1 | 4/2004 | Gellman et al. |
| 6,719,765 B2 | 4/2004 | Bonutti |
| 6,743,239 B1 | 6/2004 | Kuehn et al. |
| 6,743,240 B2 | 6/2004 | Smith et al. |
| 6,755,843 B2 | 6/2004 | Chung et al. |
| 6,773,441 B1 | 8/2004 | Laufer et al. |
| 6,786,913 B1 | 9/2004 | Sancoff et al. |
| 6,821,285 B2 | 11/2004 | Laufer et al. |
| 6,835,200 B2 | 12/2004 | Laufer et al. |
| 6,889,116 B2 | 5/2005 | Jinno |
| 6,936,054 B2 | 8/2005 | Chu |
| 6,936,061 B2 | 8/2005 | Sasaki |
| 6,955,643 B2 | 10/2005 | Gellman et al. |
| 6,972,017 B2 | 12/2005 | Smith et al. |
| 6,981,628 B2 | 1/2006 | Wales |
| 6,991,635 B2 | 1/2006 | Takamoto et al. |
| 6,997,931 B2 | 2/2006 | Sauer et al. |
| 7,011,668 B2 | 3/2006 | Sancoff et al. |
| 7,037,315 B2 | 5/2006 | Sancoff et al. |
| 7,037,324 B2 | 5/2006 | Martinek |
| 7,041,111 B2 | 5/2006 | Chu |
| 7,052,489 B2 | 5/2006 | Griego et al. |
| RE39,152 E | 6/2006 | Aust et al. |
| 7,063,710 B2 | 6/2006 | Takamoto et al. |
| 7,063,715 B2 | 6/2006 | Onuki et al. |
| 7,107,124 B2 | 9/2006 | Green |
| 7,153,314 B2 | 12/2006 | Laufer et al. |
| 7,191,900 B2 | 3/2007 | Opie et al. |
| 7,192,437 B2 | 3/2007 | Shalaby |
| 7,211,093 B2 | 5/2007 | Sauer et al. |
| 7,218,972 B2 | 5/2007 | Rodriguez |
| 7,232,448 B2 | 6/2007 | Battles et al. |
| 7,244,260 B2 | 7/2007 | Koseki |
| 7,248,944 B2 | 7/2007 | Green |
| 7,468,068 B2 | 12/2008 | Kolster |
| 7,601,164 B2 | 10/2009 | Wu |
| 7,645,284 B2 | 1/2010 | Burbank et al. |
| 7,666,194 B2 | 2/2010 | Field et al. |
| 7,691,112 B2 | 4/2010 | Chanduszko et al. |
| 7,704,261 B2 | 4/2010 | Sakamoto et al. |
| 7,708,747 B2 | 5/2010 | Bjerken |
| 7,722,630 B1 | 5/2010 | Stone et al. |
| 7,731,726 B2 | 6/2010 | Belhe et al. |
| 7,736,372 B2 | 6/2010 | Reydel et al. |
| 7,758,597 B1 | 7/2010 | Tran et al. |
| 7,758,598 B2 | 7/2010 | Conlon et al. |
| 7,766,925 B2 | 8/2010 | Stokes et al. |
| 7,771,438 B2 | 8/2010 | Dreyfuss et al. |
| 7,776,059 B2 | 8/2010 | Craig |
| 7,776,066 B2 | 8/2010 | Onuki et al. |
| 7,780,701 B1 | 8/2010 | Meridew et al. |
| 7,784,612 B2 | 8/2010 | Kanda et al. |
| 7,798,325 B2 | 9/2010 | Wizemann et al. |
| 7,814,630 B2 | 10/2010 | Price et al. |
| 7,815,654 B2 | 10/2010 | Chu |
| 7,815,659 B2 | 10/2010 | Conlon et al. |
| 7,828,812 B2 | 11/2010 | Stokes et al. |
| 7,833,235 B2 | 11/2010 | Chu |
| 7,833,237 B2 | 11/2010 | Sauer |
| 7,837,696 B2 | 11/2010 | Modesitt et al. |
| 7,842,047 B2 | 11/2010 | Modesitt et al. |
| 7,842,048 B2 | 11/2010 | Ma |
| 7,846,170 B2 | 12/2010 | Modesitt et al. |
| 7,850,701 B2 | 12/2010 | Modesitt et al. |
| 7,883,517 B2 | 2/2011 | Pantages et al. |
| 7,883,519 B2 | 2/2011 | Oren et al. |
| 7,887,554 B2 | 2/2011 | Stokes et al. |
| 7,935,128 B2 | 5/2011 | Rioux et al. |
| 7,947,052 B2 | 5/2011 | Baxter, III et al. |
| 7,947,053 B2 | 5/2011 | McKay et al. |
| 7,951,157 B2 | 5/2011 | Gambale |
| 7,967,832 B2 | 6/2011 | Chu |
| 7,967,842 B2 | 6/2011 | Bakos |
| 7,972,344 B2 | 7/2011 | Murray et al. |
| 7,976,552 B2 | 7/2011 | Suzuki |
| 8,628,545 B2 | 1/2014 | Cabrera et al. |
| 2002/0010480 A1 | 1/2002 | Sancoff et al. |
| 2002/0065526 A1 | 5/2002 | Oren et al. |
| 2002/0072702 A1 | 6/2002 | Quay |
| 2002/0128666 A1 | 9/2002 | Sancoff et al. |
| 2002/0173800 A1 | 11/2002 | Dreyfuss et al. |
| 2002/0198542 A1 | 12/2002 | Yamamoto et al. |
| 2003/0009195 A1 | 1/2003 | Field et al. |
| 2003/0014077 A1 | 1/2003 | Leung et al. |
| 2003/0045891 A1 | 3/2003 | Yamamoto et al. |
| 2003/0105475 A1 | 6/2003 | Sancoff et al. |
| 2003/0105476 A1 | 6/2003 | Sancoff et al. |
| 2003/0114863 A1 | 6/2003 | Field et al. |
| 2003/0116670 A1 | 6/2003 | Gentry |
| 2003/0171761 A1 | 9/2003 | Sancoff et al. |
| 2003/0233104 A1 | 12/2003 | Gellman et al. |
| 2004/0010245 A1 | 1/2004 | Cerier et al. |
| 2004/0060410 A1 | 4/2004 | Leung et al. |
| 2004/0068272 A1 | 4/2004 | Sauer et al. |
| 2004/0087976 A1 | 5/2004 | DeVries et al. |
| 2004/0092967 A1 | 5/2004 | Sancoff et al. |
| 2004/0181243 A1 | 9/2004 | Chu et al. |
| 2004/0193186 A1 | 9/2004 | Kortenbach et al. |
| 2004/0199184 A1 | 10/2004 | Topper et al. |
| 2005/0043747 A1 | 2/2005 | Field et al. |
| 2005/0085832 A1 | 4/2005 | Sancoff et al. |
| 2005/0096694 A1 | 5/2005 | Lee |
| 2005/0126876 A1 | 6/2005 | Simmons |
| 2005/0165419 A1 | 7/2005 | Sauer et al. |
| 2005/0256533 A1 | 11/2005 | Roth et al. |
| 2006/0025817 A1 | 2/2006 | Ortiz et al. |
| 2006/0036232 A1 | 2/2006 | Primavera et al. |
| 2006/0069396 A1 | 3/2006 | Meade et al. |
| 2006/0111209 A1 | 5/2006 | Hinman et al. |
| 2006/0235304 A1 | 10/2006 | Harhen et al. |
| 2006/0253126 A1 | 11/2006 | Bjerken et al. |
| 2006/0282093 A1 | 12/2006 | Shelton, IV et al. |
| 2007/0005110 A1 | 1/2007 | Collier et al. |
| 2008/0188868 A1 | 8/2008 | Weitzner et al. |
| 2008/0221392 A1 | 9/2008 | Jorgensen |
| 2008/0249364 A1 | 10/2008 | Korner |
| 2008/0255421 A1 | 10/2008 | Hegeman et al. |
| 2008/0312688 A1 | 12/2008 | Nawrocki et al. |
| 2017/0360431 A1* | 12/2017 | Baril ............... A61B 17/0625 |

FOREIGN PATENT DOCUMENTS

| | | |
|---|---|---|
| EP | 0647431 A2 | 4/1995 |
| EP | 1329194 A1 | 7/2003 |
| EP | 1481628 A1 | 12/2004 |
| EP | 1915957 A2 | 4/2008 |
| EP | 1915966 A1 | 4/2008 |
| EP | 2044890 A1 | 4/2009 |
| EP | 2263558 A2 | 12/2010 |
| EP | 2792306 A2 | 10/2014 |
| EP | 3175798 A1 | 6/2017 |
| WO | 9811814 A2 | 3/1998 |
| WO | 9811829 A1 | 3/1998 |
| WO | 9853745 A1 | 12/1998 |
| WO | 9915090 A1 | 4/1999 |
| WO | 9918859 A1 | 4/1999 |
| WO | 0067834 A1 | 11/2000 |

(56) References Cited

FOREIGN PATENT DOCUMENTS

| WO | 0174254 A1 | 10/2001 |
| WO | 0234147 A1 | 5/2002 |
| WO | 03017850 A2 | 3/2003 |
| WO | 2006061868 A1 | 6/2006 |
| WO | 2008042423 A2 | 4/2008 |
| WO | 2008045333 A2 | 4/2008 |

OTHER PUBLICATIONS

European Search Report for EP 07839357.6 date of completion Oct. 31, 2012 (10 pgs.).
European Search Report for EP12169361.8 dated Aug. 6, 2012.
European Search Report for EP 09251544.4-1659 date of completion is Feb. 21, 2013 (18 pages).
Extended European Search Report issued in European Patent Application No. 19181509.1, dated Nov. 15, 2019.
Extended European Search Report issued in EP Application No. 19190127.1, dated Dec. 19, 2019.

* cited by examiner

NEEDLE RELOAD DEVICE FOR USE WITH ENDOSTITCH DEVICE

CROSS-REFERENCE TO RELATED APPLICATION

This application claims the benefit of and priority to U.S. Provisional Patent Application No. 62/714,781 filed Aug. 6, 2018, the entire disclosure of which is incorporated by reference herein.

BACKGROUND

Technical Field

The present disclosure relates to devices for suturing or stitching and, more particularly, to a needle reload device for endoscopic suturing and/or stitching through an access tube or the like.

Background

One of the advances in recent years to reduce the invasiveness of surgical procedures is endoscopic surgery. Generally, endoscopic surgery involves incising through body walls. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas.

In many surgical procedures, including those involved in endoscopic surgery, it is often necessary to suture bodily organs or tissue. Suturing requires loading or unloading needles to endoscopic suturing or stitching devices. Accordingly, a need exists for simple and effective method and apparatus for loading or unloading needles to or from endoscopic suturing or stitching devices.

SUMMARY

The present disclosure describes a needle reload device for use with an endoscopic stitching device that demonstrates a practical approach to meeting the performance requirements and overcoming usability challenges associated with reloading suture needles to the endoscopic stitching device. In accordance with an embodiment of the present disclosure, there is provided a needle reload device for use with an endoscopic stitching device including a base portion and a loading assembly. The base portion includes a tool receiving portion configured to receive a tool assembly of the endoscopic stitching device. The loading assembly is disposed within the base portion. The loading assembly includes a needle holder pulley rotatably supported with the base portion, and a needle release arm. The needle holder pulley includes a base including first and second portions configured to detachably receive a suture needle. The needle release arm is transitionable between an engaged state, in which, the needle release arm engages the needle holder pulley to inhibit rotation of the needle holder pulley, and a disengaged state, in which, the needle release arm is disengaged from the needle holder pulley such that the needle holder pulley is rotatable. When the needle release arm is in the engaged state, the first portion of the needle holder pulley is positioned between jaws of the tool assembly of the endoscopic stitching device disposed in the tool receiving portion of the base portion, and when the needle release arm is in the disengage state, the second portion of the base of the needle holder pulley is positioned between the jaws of the tool assembly disposed in the tool receiving portion of the base portion.

In an embodiment, the needle holder pulley may include an axle rotatably supported in the base portion. The base of the needle holder pulley may extend radially outward from the axle for concomitant rotation therewith.

In another embodiment, the first and second portions of the base of the needle holder pulley may define respective first and second slits dimensioned to detachably receive the suture needle.

In yet another embodiment, the base portion may include a central guide positioned to limit axial displacement of the jaws of the tool assembly when the jaws are received in the tool receiving portion of the base portion.

In still yet another embodiment, the base of the needle holder pulley may be axially aligned with the central guide of the base portion.

In still yet another embodiment, the needle release arm of the loading assembly may include a sliding portion defining an arc. The base portion may define a groove corresponding to the arc of the sliding portion of the needle release arm.

In still yet another embodiment, the arc defined by the sliding portion of the needle release arm may correspond to an arc defined by the jaws of the tool assembly when the jaws are transitioned between open and closed positions.

In an embodiment, the sliding portion of the needle release arm of the loading assembly may include a stop configured to engage the needle holder pulley to inhibit rotation of the needle holder pulley, and may define a notch dimensioned to receive at least a portion of the needle holder pulley therethrough to enable rotation of the base of the needle holder pulley.

In another embodiment, the needle release arm may include a tongue configured to engage one of the jaws such that when the jaws transition from a closed position to an open position, the one of the jaws causes the tongue to slide transversely outward.

In yet another embodiment, the loading assembly may further include a biasing member coupled to the base portion and the needle holder pulley such that the needle holder pulley is biased to place the second portion of the base between the jaws when the needle release arm is in the disengaged state.

In yet another embodiment, the base portion may further include a spool receiving portion configured to receive a spool wound with a suture.

In still yet another embodiment, the base portion may further include an engaging portion including side walls defining a groove therebetween. The groove may be dimensioned to receive at least a portion of an elongate shaft assembly of the endoscopic stitching device.

In accordance with another embodiment of the present disclosure, there is provided a suturing kit including an endoscopic stitching device and a needle reload device. The endoscopic stitching device includes an elongate shaft assembly including a tool assembly having first and second jaws transitionable between open and closed positions. The needle reload device includes a base portion including a tool receiving portion configured to receive the tool assembly of the endoscopic stitching device and a loading assembly disposed within the base portion. The loading assembly includes a needle holder pulley rotatably supported with the base portion, and a needle release arm. The needle holder pulley includes a base including first and second portions configured to detachably receive a suture needle. The needle release arm is transitionable between an engaged state, in which the needle release arm engages the needle holder pulley to inhibit rotation of the needle holder pulley, and a disengaged state, in which the needle holder pulley is rotatable. When the needle release arm is in the engaged state, the first portion of the needle holder pulley is positioned between the first and second jaws of the tool assembly of the endoscopic stitching device, and when the needle release arm is in the disengage state, the second portion of the base of the needle holder pulley is positioned between the first and second jaws of the tool assembly.

DETAILED DESCRIPTION OF THE DRAWINGS

The foregoing objects, features and advantages of the disclosure will become more apparent from a reading of the following description in connection with the accompanying drawings, in which.

DETAILED DESCRIPTION

Figure 1:
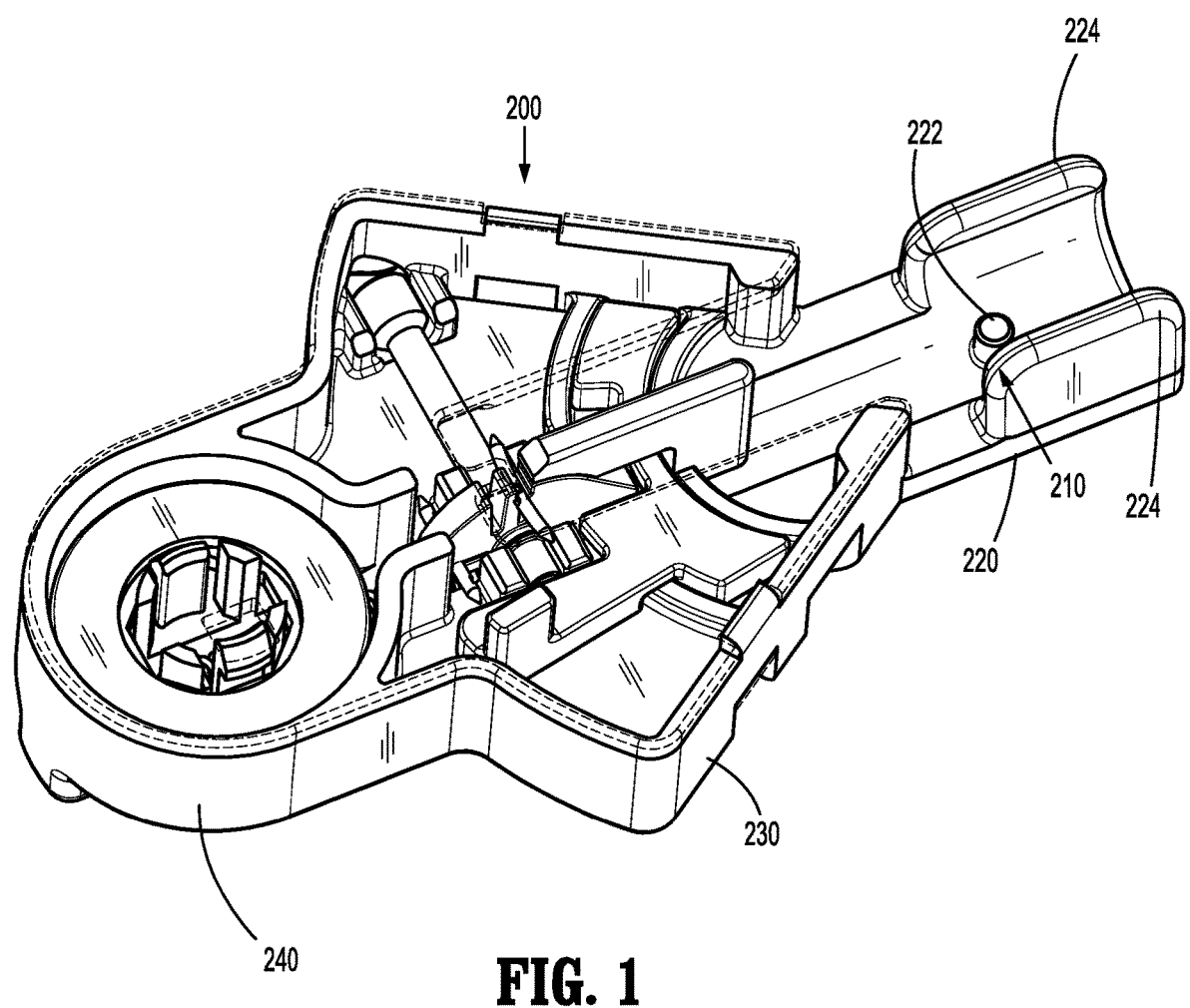
FIG. 1 is a perspective view of a needle reload device for use with an endoscopic stitching device in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

Figure 6:
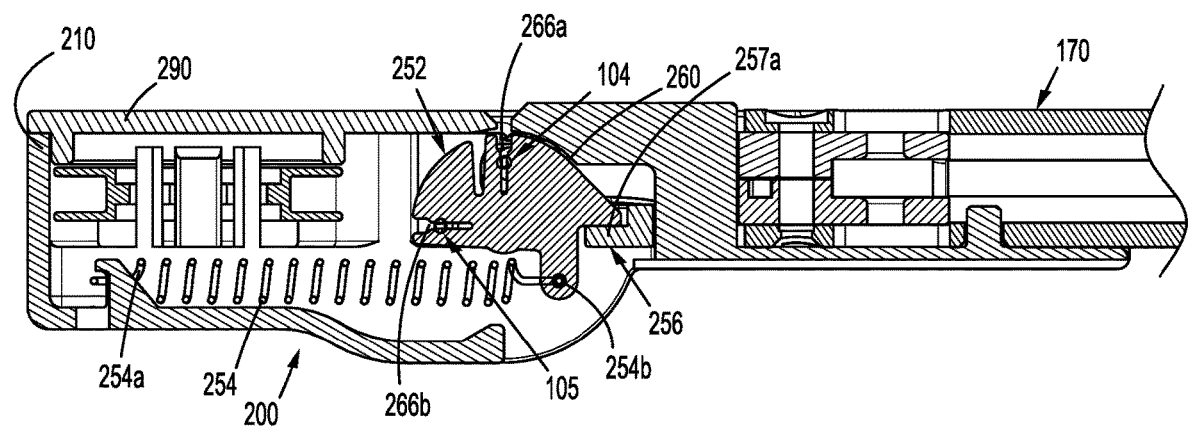
FIGS. 6 and 7 are side cross-sectional views of the needle reload device and the tool assembly of FIG. 5 illustrating use.

With reference to FIG. 1, a needle reload device for use with a stitching device in accordance with an embodiment of the present disclosure is shown generally as a needle reload device 200. The needle reload device 200 is adapted to be particularly useful in endoscopic or laparoscopic procedures, wherein an endoscopic portion of the stitching device such as, e.g., a tool assembly 120 (FIG. 2), is insertable into an operative site, via a cannula assembly or the like (not shown). In particular, the needle reload device 200 is configured to facilitate swapping of a used needle 104 (FIG. 6) with a new needle 105 (FIG. 6). The stitching device may include a handle assembly (not shown) and an elongate shaft assembly 170 (FIG. 3) extending distally from the handle assembly and including the tool assembly 120. It is contemplated that the needle reload device 200 may be used with a powered endoscopic stitching device including a powered handle assembly electro-mechanically actuating the tool assembly 120, or an endoscopic stitching device including a manually operated handle assembly mechanically actuating the tool assembly 120.

Figure 2:
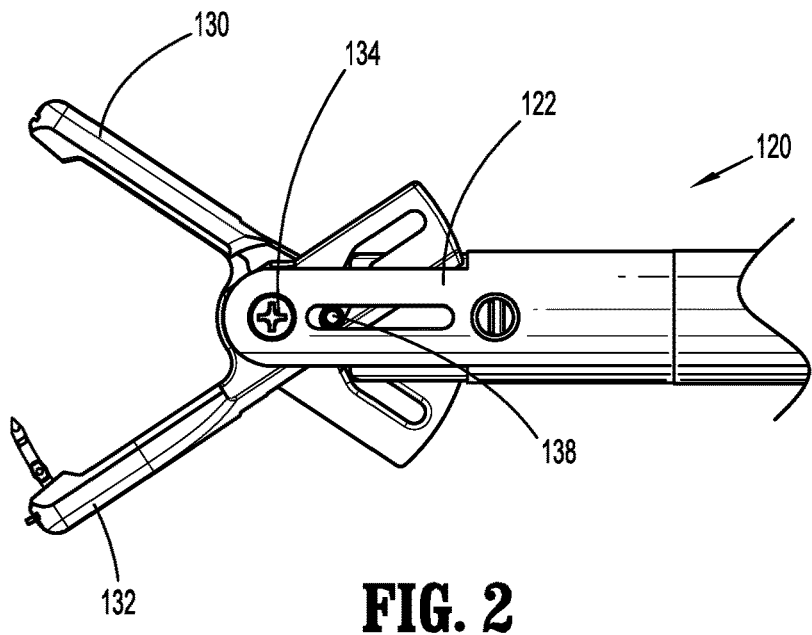
FIG. 2 is a partial top view of an elongate shaft assembly of the endoscopic stitching device.
Figure 3:
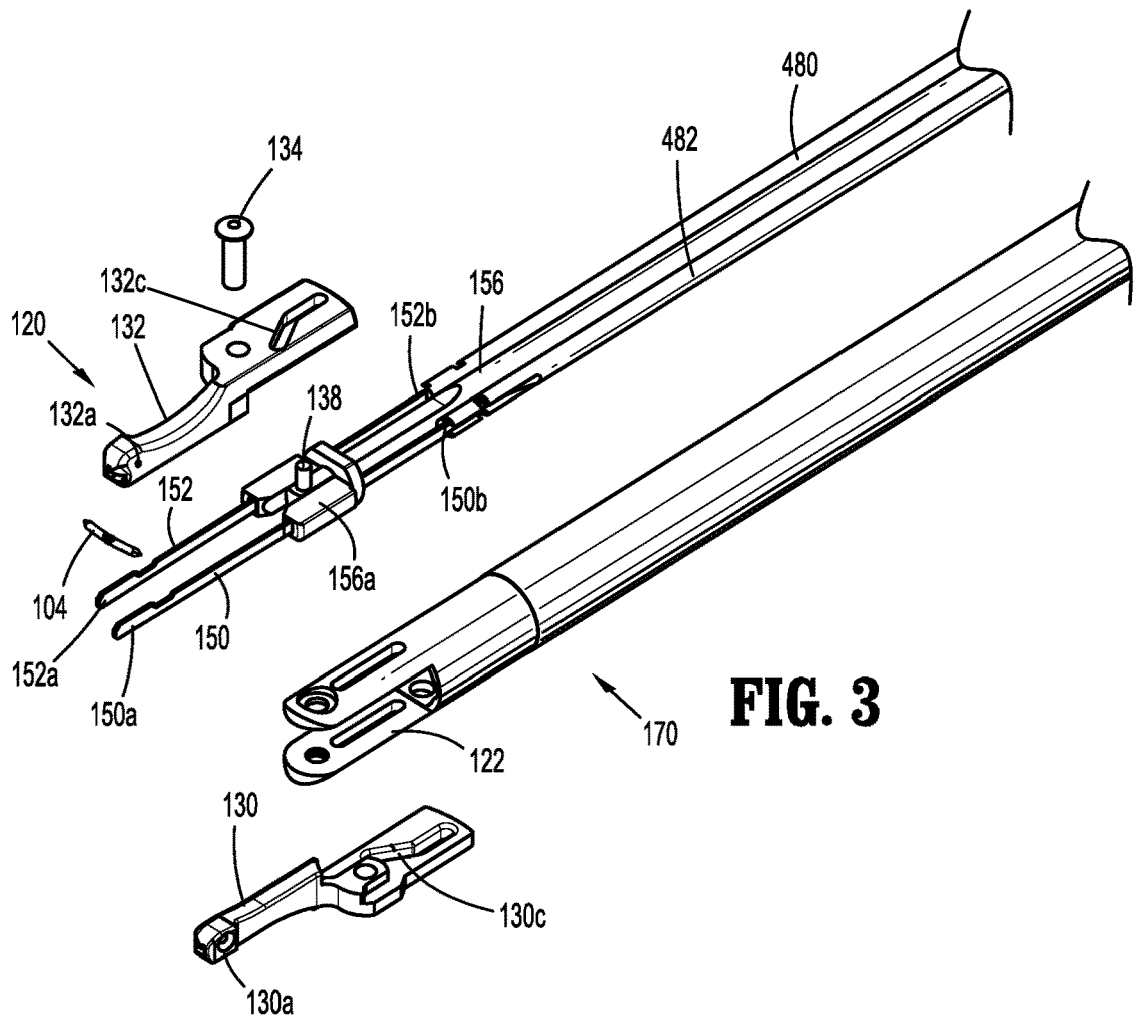
FIG. 3 is a perspective view, with parts separated, of the elongate shaft assembly of FIG. 3.

With reference now to FIGS. 2 and 3, the tool assembly 120 of the endoscopic stitching device includes a support member 122 and jaws 130, 132 pivotably mounted on the support member 122 by means of a jaw pivot pin 134. To move the jaws 130, 132 between an open position and a closed position, the main rod 156 is operatively coupled to the jaws 130, 132. In particular, the main rod 156 has a camming pin 138 mounted at a distal end 156a thereof. The camming pin 138 rides in angled camming slots 130c, 132c defined in the respective jaws 130, 132 such that axial or longitudinal movement of the main rod 156 causes the jaws 130, 132 to be cammed between open and closed positions. The main rod 156 may be provided with, e.g., biasing members in the form of a return spring, to bias the main rod 156 toward an initial position, in which, e.g., the jaws 130, 132 are in the open position.

Figure 4:
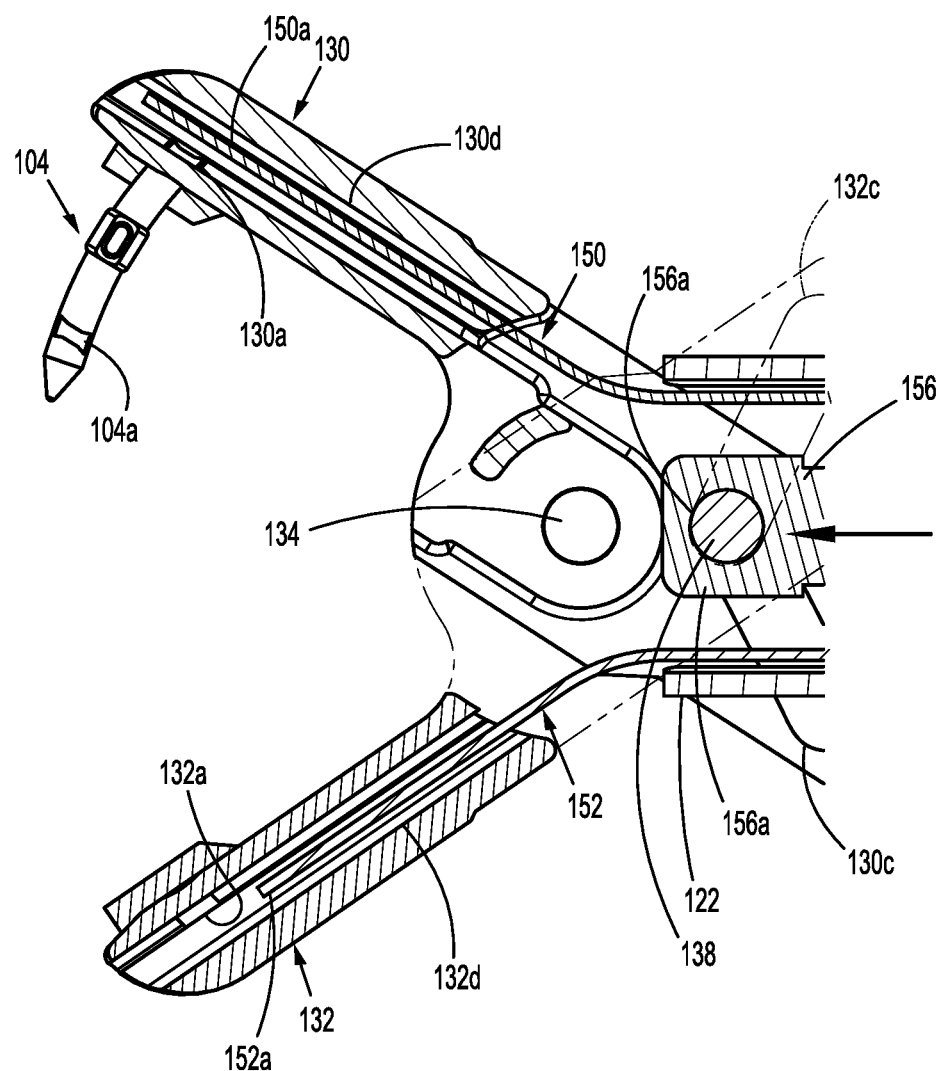
FIG. 4 is a partial, longitudinal cross-sectional view of the tool assembly of FIG. 2.

With reference to FIGS. 3 and 4, the tool assembly 120 further includes a pair of needle engaging members or blades 150, 152 which are slidably supported within the support member 122. Each blade 150, 152 includes a distal end 150a or 152a slidably extending into a blade receiving channel 130d or 132d of the corresponding jaw 130 or 132, and a proximal end 150b or 152b operatively coupled to a corresponding first or second blade drive member 480 or 482 extending through the elongate shaft assembly 170 and operatively coupled to the handle assembly 200. The first and second blade drive members 480, 482 are coupled with the respective blades 150, 152, such that reciprocating axial displacement of the first and second blade drive members 480, 482 provides reciprocating axial displacement of the blades 150, 152, enabling swapping of a needle 104 between the jaws 130, 132.

With particular reference to FIG. 4, the blade receiving channels 130d, 132d are dimensioned to at least partially intersect needle recesses 130a, 132a. Thus, by advancing the blade 150 or 152 within the corresponding blade receiving channel 130d or 132d, the distal end 150a or 152a of the corresponding blade 150 or 152 engages or "locks in" a groove 104a formed in the needle 104 when at least a portion of the needle 104 is received within the corresponding recess 130a or 132a. A suture (not shown) may be secured to the needle 104. The suture may include a plurality of barbs oriented to resist movement in a direction opposite to the direction of travel.

The stitching device is transitionable between a suture mode and a reload mode. In the suture mode, the first and second jaws 130, 132 are in the open position and the needle 104 is loaded and held in one jaw 130 or 132. The first and second jaws 130, 132 may be positioned about or over a target tissue and an actuation switch or a manual trigger may be actuated or squeezed to approximate the first and second jaws 130, 132. As the first and second jaws 130, 132 are approximated, the exposed end of the needle 104 is penetrated through the target tissue and enters opposed jaw 130 or 132. In order to perform suturing, the needle 104 is swapped between the first and second jaws 130, 132 through reciprocating axial displacement of the first and second blade drive members 480, 482 in opposite directions. As a result, the first and second blade drive members 480, 482 are axially displaced in opposite directions, which, in turn, causes reciprocating axial displacement of the blades 150, 152 of the tool assembly 120. In so doing, the needle 104 is swapped from one blade 150 or 152 to the other blade 150 or 152 when the actuation switch or the manual trigger is released, whereby the needle 104 is loaded or held in the other jaw 130 or 132.

In the reload mode, a loading or unloading of the needle 104 into or from one of the first and second jaws 130, 132 may be performed. Specifically, the clinician may press a needle reload switch, which retracts both blades 150, 152 such that notches formed in respective blades 150, 152 are aligned with or in registration with the respective needle recesses 130a, 132a defined in the respective first and second jaws 130, 132. With the notches of the blades 150, 152 aligned with or in registration with the respective needle recesses 130a, 132a, the needle 104 may be loaded into a selected one needle recess 130a, 132a of the first and second jaws 130, 132 or unloaded from the needle recesses 130a, 132a of the first and second jaws 130, 132. Reference may be made to U.S. Pat. No. 8,628,545, entitled "Endoscopic Stitching Devices," the entire contents of which are incorporated herein by reference, for a detailed description of the construction and operation of a tool assembly.

Figure 5:
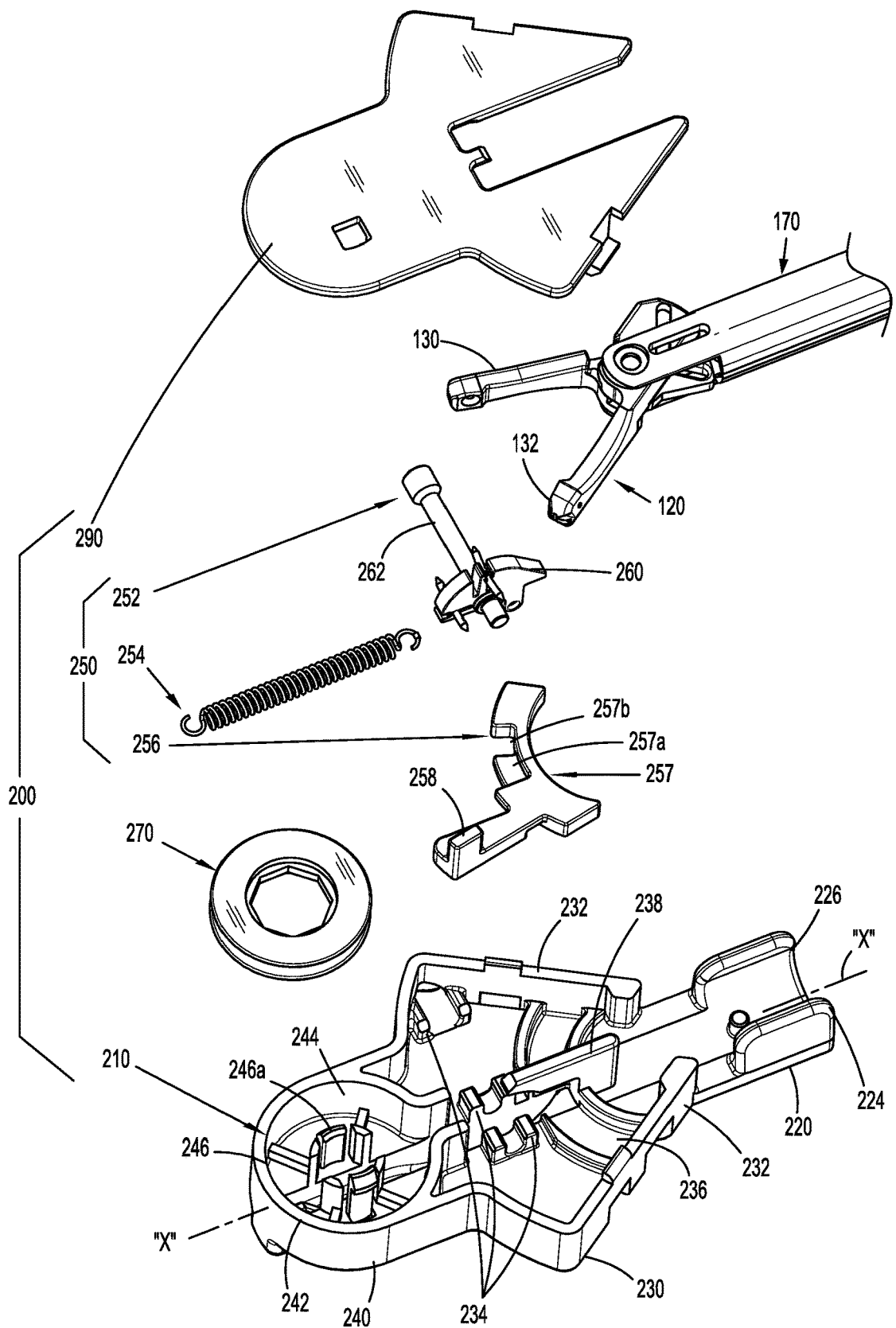
FIG. 5 is an exploded perspective view, with parts separated, of the needle reload device of FIG. 1 and a tool assembly of FIG. 2.

With reference now to FIG. 5, the needle reload device 200 includes a base portion 210, a loading assembly 250 operatively disposed within the base portion 210, and a cover 290 in superposed relation with the base portion 210. The base portion 210 includes an engaging portion 220, a tool receiving portion 230 extending distally from the engaging portion 220, and a spool receiving portion 240 extending distally from the tool receiving portion 230. The engaging portion 220 defines a groove 226 dimensioned to guide and receive at least a portion of the elongate shaft assembly 170. In particular, the engaging portion 220 may further include a boss 222 (FIG. 1) configured to engage a bore (not shown) defined in the elongate shaft assembly 170 in order to align and further enhance securement of the elongate shaft assembly 170 to the base portion 210. The engaging portion 220 may further include side walls 224 to further facilitate insertion of at least a portion of the elongate shaft assembly 170 therebetween.

The tool receiving portion 230 is configured to receive the tool assembly 120 of the elongate shaft assembly 170. The tool receiving portion 230 includes peripheral guides 232 dimensioned to receive first and second jaws 130, 132 of the tool assembly 120 therebetween. The peripheral guides 232 define an arc extending transversely outward with respect to a longitudinal axis "X-X" defined by the base portion 210. In particular, the tool receiving portion 230 may be proximally tapered corresponding to an arc defined by the first and second jaws 130, 1320 when the first and second jaws 130, 132 are transitioned between the closed and open positions.

With reference now to FIGS. 5 and 6, the tool receiving portion 230 is configured to receive the loading assembly 250 therein. In particular, the tool receiving portion 230 includes rotation supports 234 configured to rotatably support a needle holder pulley 252 of the loading assembly 250. The tool receiving portion 230 further includes a groove 236 configured to slidably receive at least a portion of a needle release arm 256 of the loading assembly 250. In particular, the needle release arm 256 includes a sliding portion 257 slidably disposed in the groove 236 defining an arc or having an arcuate shape. The tool receiving portion 230 further includes a central guide 238 configured to limit axial displacement of the first and second jaws 130, 132 when the first and second jaws 130, 132 are received in the tool receiving portion 230. To this end, the central guide 238 is interposed between the first and second jaws 130, 132 when the first and second jaws 130, 132 are received in the tool receiving portion 230.

With particular reference to FIG. 5, the spool receiving portion 240 includes an annular wall 242 defining a cavity 244 therein. The spool receiving portion 240 includes a core 246 including a plurality of circumferentially arranged resilient fingers 246a configured to rotatably support an annular suture spool 270 including suture (not shown).

With continued reference to FIGS. 5 and 6, the needle reload device 200 is configured to automate the process of swapping the used needle 104 with the new needle 105. To this end, the needle reload device 200 includes the loading assembly 250. The loading assembly 250 includes the needle holder pulley 252, a biasing member 254, and the needle release arm 256 selectively engageable with the needle holder pulley 252. In particular, the needle holder pulley 252 includes an axle 262 rotatably supported on the rotation supports 234 of the tool receiving portion 230 of the base portion 210. The needle holder pulley 252 further includes a base 260 having, e.g., an arcuate, shape. The base 260 extends radially outward from the axle 262 for concomitant rotation therewith. The base 260 includes first and second slits 266a, 266b dimensioned to receive the respective needles 104, 105. The needle holder pulley 252 is rotatable about an axis defined by the axle 262 such that as the base 260 rotates, orientation or position of the first and second slits 266a, 266b changes relative to the tool receiving portion 230 or the first and second jaws 130, 132 disposed in the tool receiving portion 230. In this manner, based on the rotation of the axle 262 or the base 260, the first and second jaws 130, 132 of the tool assembly 120 may selectively engage the first and second slits 266a, 266b (FIG. 6), as will be discussed below.

With continued reference to FIGS. 5 and 6, the needle release arm 256 of the loading assembly 250 includes a sliding portion 257 slidably disposed in the groove 236 of the base portion 210. The groove 236 may define an arc configured to enable sliding movement of the sliding portion 257 defining a corresponding arc. In particular, the arc defined by the groove 236 and the sliding portion 257 corresponds to the arc defined by the first and second jaws 130, 132 of the tool assembly 120, when the first and second jaws 130, 132 transition between the closed and open positions. The needle release arm 256 further includes a tongue 258 configured to engage the second jaw 132 when the first and second jaws 130, 132 transition from the closed position to the open position. The second jaw 132 engages the tongue 258 and imparts transversely outward movement to the tongue 258, which, in turn, causes concomitant sliding of the sliding portion 257.

The sliding portion 257 of the needle release arm 256 includes a stop portion 257a and defines a notch 257b. Under such a configuration, based on the position of the needle release arm 256, the base 260 of the needle holder pulley 252 may engage the stop portion 257a of the needle release arm 256, which inhibits rotation of the base 260. However, the needle release arm 256 may be positioned such that at least a portion of the base 260 rotates through the notch 257b defined in the sliding portion 257 of the needle release arm 256, thereby enabling rotation of the base 260 of the needle holder pulley 252, which, in turn, causes the base 260 to align the second slit 266b holding the new needle 105 (FIG. 7) between the first and second jaws 130, 132 disposed in the tool receiving portion 230. In addition, such a movement is facilitated by a biasing member 254.

With particular reference to FIG. 6, a first end 254*a* of the biasing member 254 is affixed to the base portion 210 and a second end 254*b* of the biasing member 254 is affixed to the base 260 of the needle holder pulley 252 such that the needle holder pulley 252 is biased to rotate when at least a portion of the base 260 of the needle holder pulley 252 extends through the notch 257*b* (FIG. 5) of the sliding portion 257. Under such a configuration, the new needle 105 is positioned between the first and second jaws 130, 132.

The used needle 104 held between the first and second jaws 130, 132 may be received in the first slit 266*a* defined in the base 260 of the needle holder pulley 252 by placing the closed first and second jaws 130, 132 in the tool receiving portion 230 and placing the used needle 104 in the first slit 266*a* defined in the base 260 of the needle holder pulley 252. At this time, the base 260 of the needle holder pulley 252 engages the stop portion 257*a* of the needle release arm 256. After the used needle 104 is received in the first slit 266*a*, the first and second jaws 130, 132 may transition from the closed position to the open position to slide the tongue 258 (FIG. 5) of the needle release arm 256 radially outward, which, in turn, slides the sliding portion 257 transversely outward such that at least a portion of the base 260 of the needle holder pulley 252 rotates through the notch 257*b* (FIG. 5) defined in the sliding portion 257 of the needle release arm 256. Such a rotation positions the new needle 105 between the first and second jaws 130, 132, and displaces the used needle 104 received in the first slit 266*a* away from the first and second jaws 130, 132.

Figure 7:
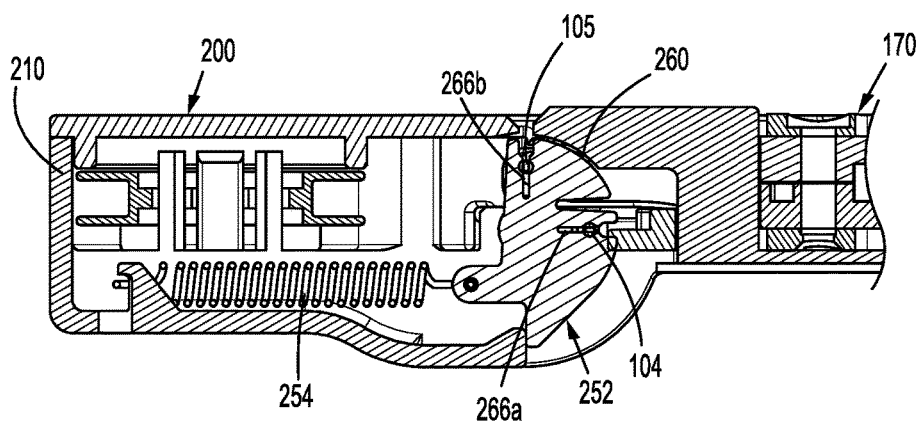

With reference now to FIGS. 6 and 7, in use, after suturing the target tissue, the needle 104 may need to be replaced or removed. To this end, the stitching device is first transitioned to the reload mode by positioning both of the blades 150, 152 (FIG. 3) of the tool assembly 120 in a distal-most position. In this manner, notches (not shown) formed in respective blades 150, 152 are aligned with or in registration with the respective needle recesses 130*a*, 132*a* (FIG. 4) defined in the respective first and second jaws 130, 132. With the notches of the blades 150, 152 aligned with or in registration with the respective needle recesses 130*a*, 132*a* of respective first and second jaws 130, 132, the needle 104 is secured with the first and second jaws 130,132. At this time, the first and second jaws 130, 132 are in the closed configuration. The tool assembly 120 is inserted in the tool receiving portion 230 of the base portion 210 of the needle reload device 200, and the elongate shaft assembly 170 is positioned in the engaging portion 220. At this time, the used needle 104 is received in the first slit 266*a* of the base 260 of the needle holder pulley 252. Thereafter, the first and second jaws 130, 132 are transitions to the open position, at which time, the second jaw 132 engages the tongue 258 (FIG. 5) of the needle release arm 256 and slidably moves the needle release arm 256 transversely outward along the arc.

In this manner, at least a portion of the base 260 (FIG. 5) of the needle holder pulley 252 extends through the notch 257*b* (FIG. 5) defined in the needle release arm 256, which in turn, causes the base 260 to rotate about the axis defined by the axle 262. Such a rotation of the base 260 places the new needle 105 in position to be received by the first and second jaws 130, 132. At this time, the first and second jaws 130, 132 may be transitioned to the closed position to receive the new needle 105 in the first and second jaws 130, 132. Upon loading the new needle 105 to the first and second jaws 130, 132, the tool assembly 120 may be removed from the needle reload device 200 and the clinician may continue to suture the target tissue.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure.

Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A needle reload device for use with an endoscopic stitching device comprising:
 a base portion including a tool receiving portion configured to receive a tool assembly of the endoscopic stitching device, and defining a groove; and
 a loading assembly disposed within the base portion, the loading assembly including:
  a needle holder pulley rotatably supported with the base portion, the needle holder pulley rotatable about an axis extending through lateral surfaces of the needle holder pulley, the needle holder pulley including a base including first and second portions configured to detachably receive a suture needle; and
  a needle release arm laterally movable relative to the needle holder pulley between an engaged state, in which, the needle release arm engages the needle holder pulley to inhibit rotation of the needle holder pulley, and a disengaged state, in which, the needle release arm is disengaged from the needle holder pulley such that the needle holder pulley is rotatable, wherein when the needle release arm is in the engaged state, the first portion of the needle holder pulley is configured to be positioned between jaws of the tool assembly of the endoscopic stitching device disposed in the tool receiving portion of the base portion, and when the needle release arm is in the disengaged state, the second portion of the base of the needle holder pulley is configured to be positioned between the jaws of the tool assembly disposed in the tool receiving portion of the base portion, wherein the needle release arm includes a sliding portion defining an arc that corresponds to the groove of the base portion.

2. The needle reload device according to claim 1, wherein the needle holder pulley includes an axle rotatably supported in the base portion, the base of the needle holder pulley extending radially outward from the axle for concomitant rotation therewith.

3. The needle reload device according to claim 2, wherein the first and second portions of the base of the needle holder pulley define respective first and second slits dimensioned to detachably receive the suture needle.

4. The needle reload device according to claim 2, wherein the base portion includes a central guide positioned to limit axial displacement of the jaws of the tool assembly when the jaws are received in the tool receiving portion of the base portion.

5. The needle reload device according to claim 4, wherein the base of the needle holder pulley is axially aligned with the central guide of the base portion.

6. The needle reload device according to claim 1, wherein the arc defined by the sliding portion of the needle release arm corresponds to an arc defined by the jaws of the tool assembly when the jaws are transitioned between open and closed positions.

7. The needle reload device according to claim 1, wherein the sliding portion of the needle release arm of the loading assembly includes a stop configured to engage the needle holder pulley to inhibit rotation of the needle holder pulley, and defines a notch dimensioned to receive at least a portion of the needle holder pulley therethrough to enable rotation of the base of the needle holder pulley.

8. The needle reload device according to claim 1, wherein the needle release arm includes a tongue configured to engage one of the jaws such that when the jaws transition from a closed position to an open position, the one of the jaws causes the tongue to slide transversely outward.

9. The needle reload device according to claim 1, wherein the loading assembly further includes a biasing member coupled to the base portion and the needle holder pulley such that the needle holder pulley is biased to place the second portion of the base between the jaws when the needle release arm is in the disengaged state.

10. The needle reload device according to claim 1, wherein the base portion further includes a spool receiving portion configured to receive a spool wound with a suture.

11. The needle reload device according to claim 1, wherein the base portion further includes an engaging portion including side walls defining a groove therebetween, the groove dimensioned to receive at least a portion of an elongate shaft assembly of the endoscopic stitching device.

12. A suturing kit comprising:
an endoscopic stitching device including an elongate shaft assembly including a tool assembly having first and second jaws transitionable between open and closed positions; and
a needle reload device including:
a base portion including a tool receiving portion configured to receive the tool assembly of the endoscopic stitching device, and defining a groove; and
a loading assembly disposed within the base portion, the loading assembly including:
a needle holder pulley rotatably supported with the base portion, the needle holder pulley rotatable about a lateral axis, the needle holder pulley including a base including first and second portions configured to detachably receive a suture needle; and
a needle release arm laterally movable relative to the needle holder pulley between an engaged state, in which, the needle release arm engages the needle holder pulley to inhibit rotation of the needle holder pulley, and a disengaged state, in which, the needle holder pulley is rotatable, wherein when the needle release arm is in the engaged state, the first portion of the needle holder pulley is positioned between the first and second jaws of the tool assembly of the endoscopic stitching device, and when the needle release arm is in the disengaged state, the second portion of the base of the needle holder pulley is positioned between the first and second jaws of the tool assembly, wherein the needle release arm of the loading assembly includes a sliding portion defining an arc, and wherein the groove of the base portion corresponds to the arc of the sliding portion of the needle release arm.

13. The suturing kit according to claim 12, wherein the loading assembly further includes a biasing member coupled to the base portion and the needle holder pulley such that the needle holder pulley is biased to place the second portion of the base of the needle holder pulley between the first and second jaws when the needle release arm is in the disengaged state.

14. The suturing kit according to claim 12, wherein the needle holder pulley includes an axle rotatably supported in the base portion, the base of the needle holder pulley extending radially outward from the axle for concomitant rotation therewith.

15. The suturing kit according to claim 12, wherein first and second portions of the base of the needle holder pulley define respective first and second slits dimensioned to detachably receive the suture needle.

16. The suturing kit according to claim 12, wherein the arc defined by sliding portion of the needle release arm corresponds to an arc defined by the first and second jaws of the tool assembly when the first and second jaws are transitioned between the open and closed positions.

17. The suturing kit according to claim 12, wherein the sliding portion of the needle release arm of the loading assembly includes a stop configured to engage the needle holder pulley to inhibit rotation of the needle holder pulley, and defines a notch dimensioned to receive at least a portion of the needle holder pulley therethrough to enable rotation of the base of the needle holder pulley.

18. The suturing kit according to claim 12, wherein the needle release arm includes a tongue configured to engage the first jaw such that when the first and second jaws transition from the closed position to the open position, the first jaw causes the tongue to slide transversely outward.

19. A needle reload device for use with an endoscopic stitching device comprising:
a base portion including a tool receiving portion configured to receive a tool assembly of the endoscopic stitching device; and
a loading assembly disposed within the base portion, the loading assembly including:
a needle holder pulley rotatably supported with the base portion, the needle holder pulley rotatable about an axis extending through lateral surfaces of the needle holder pulley, the needle holder pulley including a base including first and second portions configured to detachably receive a suture needle; and
a needle release arm laterally movable relative to the needle holder pulley between an engaged state, in which, the needle release arm engages the needle holder pulley to inhibit rotation of the needle holder pulley, and a disengaged state, in which, the needle release arm is disengaged from the needle holder pulley such that the needle holder pulley is rotatable, wherein when the needle release arm is in the engaged state, the first portion of the needle holder pulley is configured to be positioned between jaws of the tool assembly of the endoscopic stitching device disposed in the tool receiving portion of the base portion, and when the needle release arm is in the disengaged state, the second portion of the base of the needle holder pulley is configured to be positioned between the jaws of the tool assembly disposed in the tool receiving portion of the base portion, wherein the needle release arm includes a tongue configured to engage one of the jaws such that when the jaws transition from a closed position to an open position, the one of the jaws causes the tongue to slide transversely outward.

20. A suturing kit comprising:

an endoscopic stitching device including an elongate shaft assembly including a tool assembly having first and second jaws transitionable between open and closed positions; and a needle reload device including:

a base portion including a tool receiving portion configured to receive the tool assembly of the endoscopic stitching device; and a loading assembly disposed within the base portion, the loading assembly including:

a needle holder pulley rotatably supported with the base portion, the needle holder pulley rotatable about a lateral axis, the needle holder pulley including a base including first and second portions configured to detachably receive a suture needle; and a needle release arm laterally movable relative to the needle holder pulley between an engaged state, in which, the needle release arm engages the needle holder pulley to inhibit rotation of the needle holder pulley, and a disengaged state, in which, the needle holder pulley is rotatable, wherein when the needle release arm is in the engaged state, the first portion of the needle holder pulley is positioned between the first and second jaws of the tool assembly of the endoscopic stitching device, and when the needle release arm is in the disengaged state, the second portion of the base of the needle holder pulley is positioned between the first and second jaws of the tool assembly, wherein the needle release arm includes a tongue configured to engage the first jaw such that when the first and second jaws transition from the closed position to the open position, the first jaw causes the tongue to slide transversely outward.

\* \* \* \* \*